United States Patent
Bouffier et al.

(10) Patent No.: US 7,628,751 B2
(45) Date of Patent: Dec. 8, 2009

(54) MINI SUB-URETHRAL-CERVICAL SUPPORT

(75) Inventors: Bernard Bouffier, Ecole (FR); Axel Arnaud, Paris (FR)

(73) Assignee: Johnson & Johnson International, New Brunswick, NJ (US)

( * ) Notice: Subject to any disclaimer, the term of this patent is extended or adjusted under 35 U.S.C. 154(b) by 156 days.

(21) Appl. No.: 10/493,653

(22) PCT Filed: Oct. 22, 2002

(86) PCT No.: PCT/FR02/03608

§ 371 (c)(1),
(2), (4) Date: Oct. 5, 2004

(87) PCT Pub. No.: WO03/034939

PCT Pub. Date: May 1, 2003

(65) Prior Publication Data

US 2005/0107805 A1    May 19, 2005

(30) Foreign Application Priority Data

Oct. 22, 2001  (FR)  .................... 01 13585

(51) Int. Cl.
  *A61F 2/02*  (2006.01)
(52) U.S. Cl. ........................................ 600/30
(58) Field of Classification Search ............. 600/29–31, 600/37; 606/141; 128/839, 885, 897, 898
See application file for complete search history.

(56) References Cited

U.S. PATENT DOCUMENTS

| 5,013,292 | A |  | 5/1991 | Lemay |  |
|---|---|---|---|---|---|
| 5,256,133 | A |  | 10/1993 | Spitz |  |
| 5,934,283 | A |  | 8/1999 | Willem et al. |  |
| 6,068,591 | A | * | 5/2000 | Bruckner et al. | 600/30 |
| 6,908,473 | B2 | * | 6/2005 | Skiba et al. | 606/198 |
| 2002/0107430 | A1 | * | 8/2002 | Neisz et al. | 600/37 |
| 2002/0128670 | A1 |  | 9/2002 | Ulmsten et al. |  |

FOREIGN PATENT DOCUMENTS

| EP | 0684012 | 2/1995 |
|---|---|---|
| EP | 0643945 | 3/1995 |
| EP | 0755656 | 7/1996 |
| WO | WO 00/66029 | 11/2000 |
| WO | WO 00/74633 | 12/2000 |
| WO | WO 02/30293 | 4/2002 |

* cited by examiner

*Primary Examiner*—Charles A Marmor, II
*Assistant Examiner*—Christine D Hopkins
(74) *Attorney, Agent, or Firm*—Blakely, Sokoloff, Taylor & Zafman LLP

(57) ABSTRACT

The invention relates to a surgical instrument (2) that is used to implant a sub-urethral/cervical support. The invention is characterised in that it comprises at least one band (32) and two anchoring devices (2). Each of said anchoring devices (2) comprises a needle (10), the point of which supports a flexible anchoring element (22). Each of the aforementioned flexible anchoring elements (22) is connected to one end of the band (32) and each of said elements can be folded back along the length of the needle (10) when the needle is being passed through the biological tissues and subsequently deployed when said needle has cleared the tissues.

10 Claims, 6 Drawing Sheets

Figure 3:
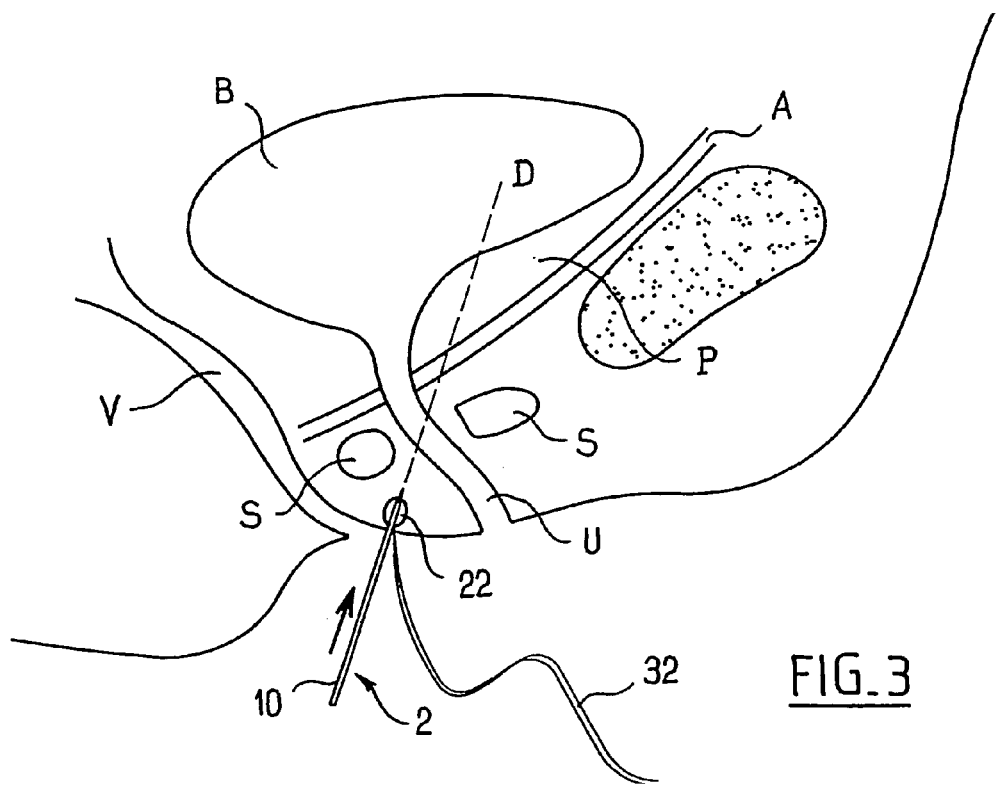

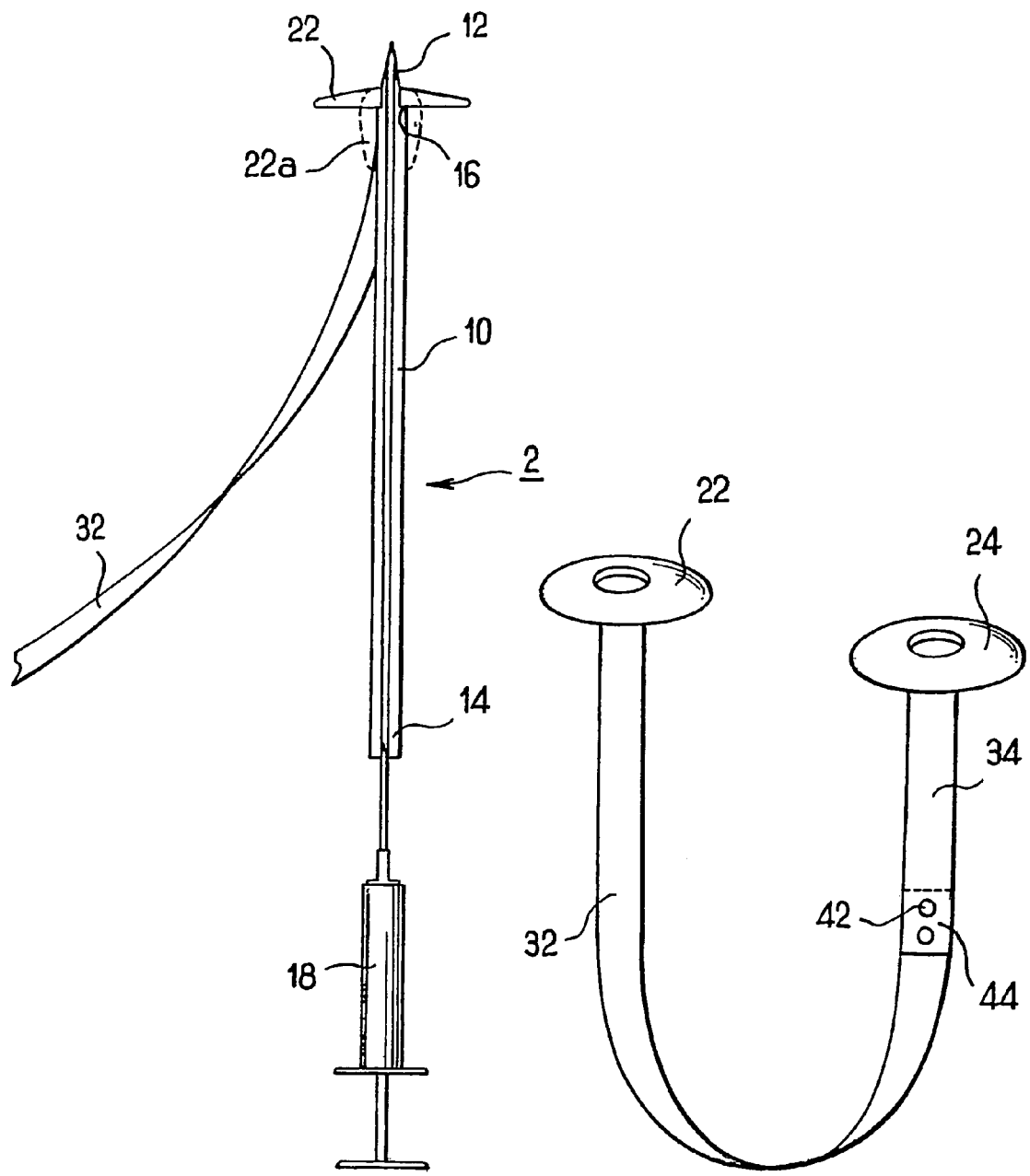
FIG_1  FIG_2

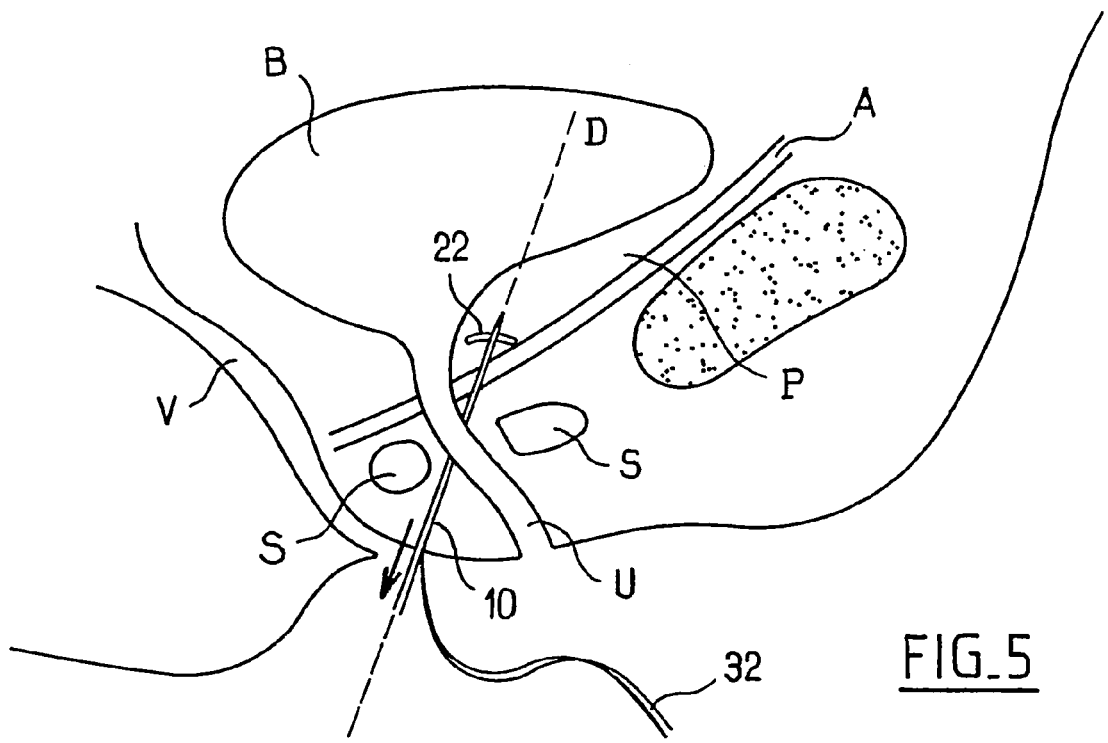
FIG_5
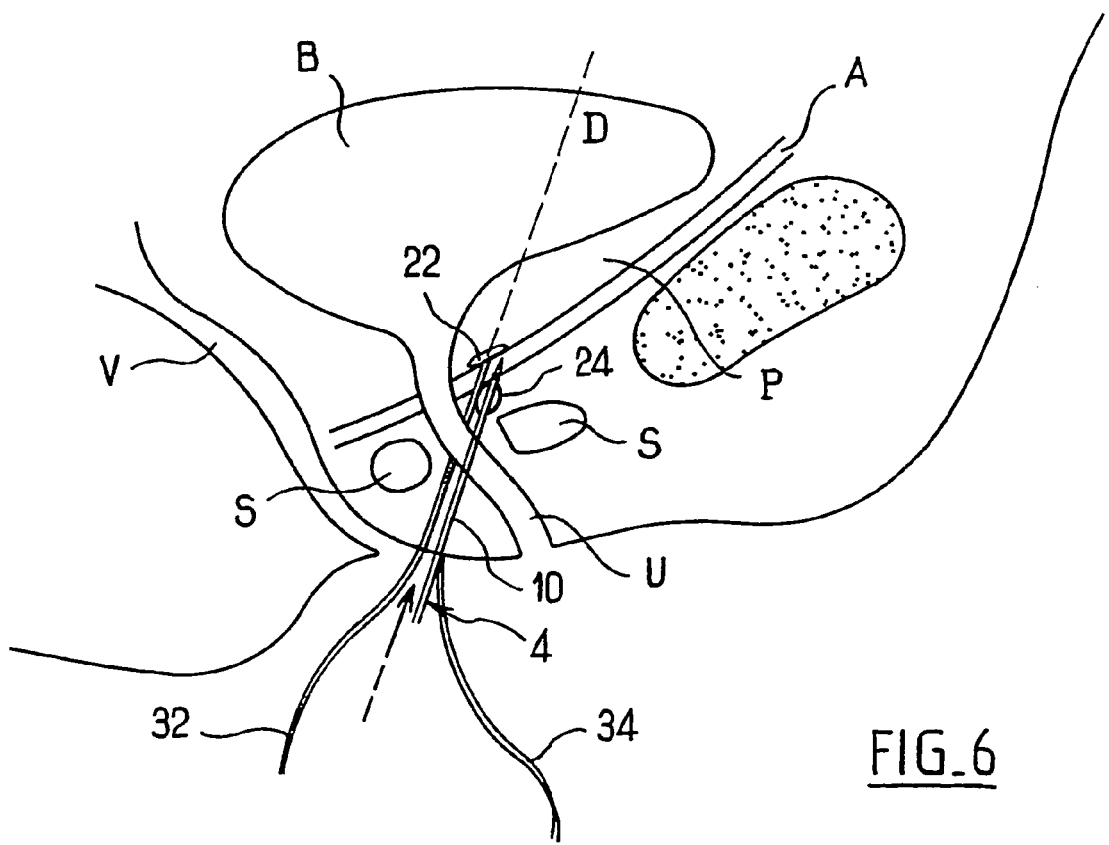
FIG_6

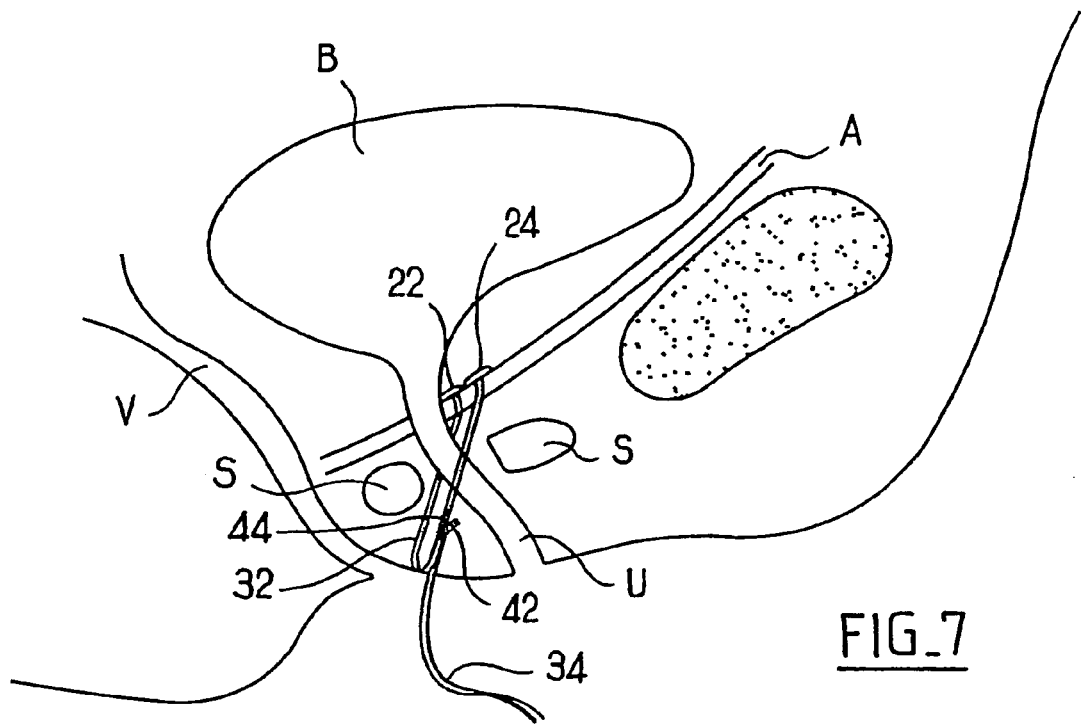
FIG_7
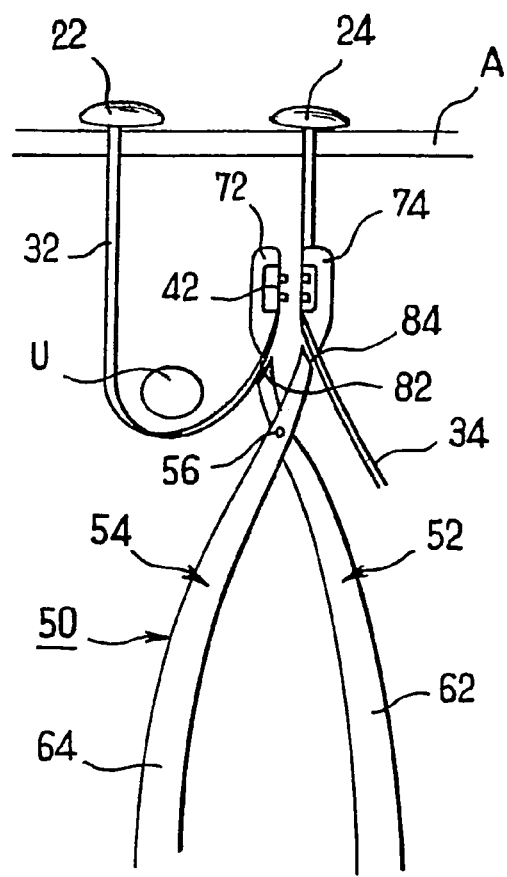
FIG_8

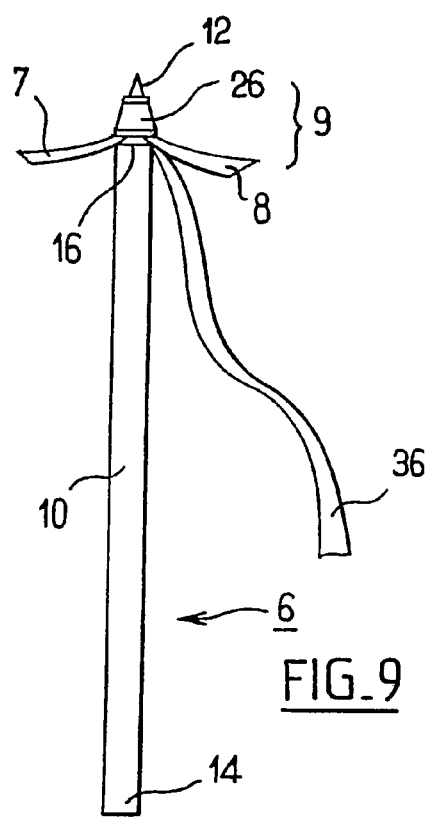
FIG_9
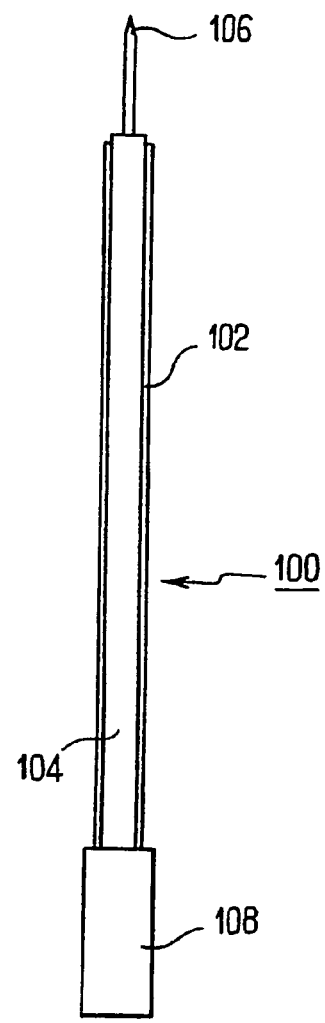
FIG_10
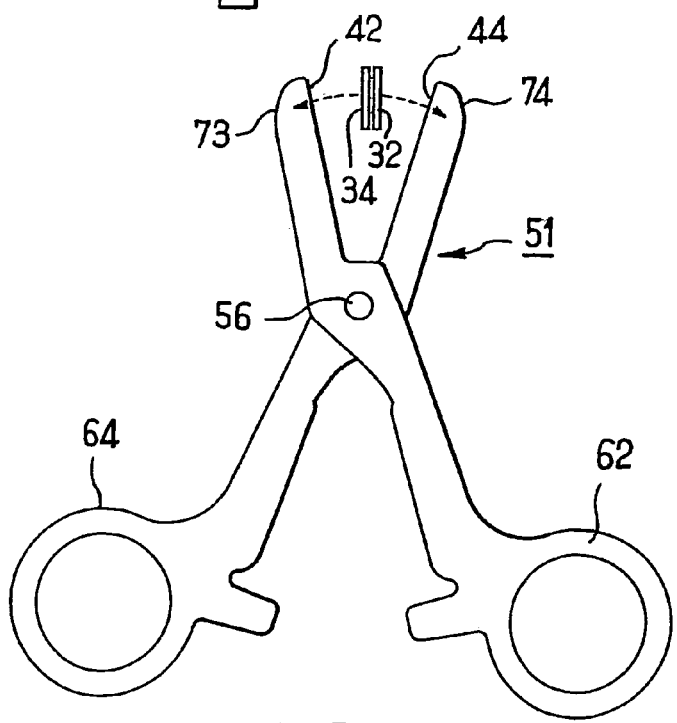
FIG_11
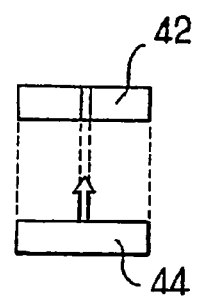
FIG_12

MINI SUB-URETHRAL-CERVICAL SUPPORT

The present patent application is a non-provisional application of International Application No. PCT/FR02/03608, filed Oct. 22, 2002.

This invention relates to the domain of urinary incontinence treatments.

Urinary incontinence in a woman may be due to relaxation of tissues or ligaments connecting the vaginal wall to the pelvic muscle and the pubis bone. These tissues or ligaments form a muscular-ligamentary and conjunctive assembly that helps to support the urethra, and cooperate with the sphincter of the urethra to actively participate in the continence mechanism under strain.

One known solution for preventing incontinence is to place a polypropylene support strip under the urethra. Document U.S. Pat. No. 5,899,909 deposited by Medscand Medical AB (Sweden) describes a surgical instrument and a process for treating incontinence in women without needing to open the abdomen. The instrument comprises two curved metallic rods and a strip, each end of the strip being connected to one of the rods. The rods are provided with removable handles that the surgeon uses to manipulate them. The surgeon inserts the rods one after the other into the vagina on each side of the urethra. Each needle is driven through the vagina wall and the venous plexus and is guided along the pubic bone to pass through the abdominal muscles. The surgeon extracts the needles from the abdominal wall. The strip automatically moves into place to form a strip around the urethra. This strip forms a reinforcing and support structure that supports the sphincter. It remains in place in the body of the patient simply due to contact forces with the tissues passed through along the length of the strip.

This type of method has the advantage that it is only very slightly invasive. This is why it is very successful.

However, when the needles are being inserted, there is a non-negligible risk that they will pass through the bladder wall. There are also risks (lesser) that the needle might damage the intestine or a blood vessel.

The purpose of this invention is to provide a device for limiting these risks. The main complications with former prosthetic systems are dominated by perforations of the bladder, blood vessels or even the intestine.

Consequently, the invention proposes a surgical instrument for implantation of a sub urethro-cervical support characterised in that it comprises at least one striplet and two anchor devices, each anchor device including a needle in which the penetrating end supports a flexible anchor element, each anchor element being connected to one end of the striplet and can be turned down over the length of the needle while the needle is passing through the biological tissues and deployed when it has passed through these tissues.

This type of instrument can advantageously be used to implant anchor elements into internal tissues of the patient's body, using needles. More particularly, the anchor elements are positioned on the fascia of pelvic muscles, which has the advantage that the needles do not need to be penetrated beyond the pubic bone and therefore there is no risk of damaging the bladder, intestines or blood vessels.

One advantage of this invention is that the support implantation operation is particularly simple and only very slightly invasive. There is no need to perforate abdominal muscles.

Another advantage of this invention is that there is no need for a cystoscopy to check the condition of the patient's bladder when carrying out the implantation operation, and this cystoscopy can introduce a risk of infection.

In one embodiment of the invention, the instrument comprises two striplets, each with one end fixed to one of the anchor elements. These striplets are inserted and guided by the needles through the wall of the vagina until the fascia of pelvic muscles, one after the other. They are then connected to each other by connection means to form a supporting loop under the urethra.

This characteristic has the advantage that the surgeon can adjust the length of the support loop. The surgeon can then precisely adjust the pressure applied by the support device under the urethra and adapt it to the patient's morphology.

In one particularly advantageous embodiment of the invention, the needle is hollow and forms a duct open at both ends, and the end of the needle that does not support the anchor element is connected to injection/suction means, for example to insert an anaesthetic product into the duct, or to insufflate a liquid facilitating the development of flexible anchor elements by moving the surrounding tissues away, or to apply suction to a part of the fluid surrounding the tip of the implantation needle in order to check the positioning of this needle.

The invention also proposes a sub urethro-cervical support device, characterised in that it comprises two anchor elements and at least one striplet, each anchor element being connected to one end of the striplet.

Figure 13:
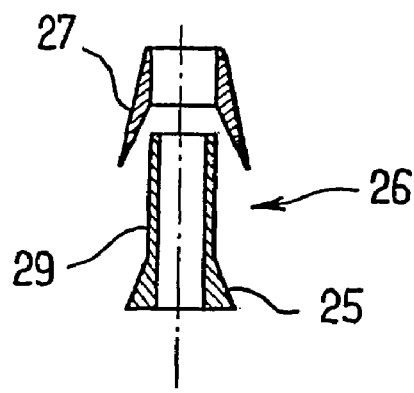
Figure 14:
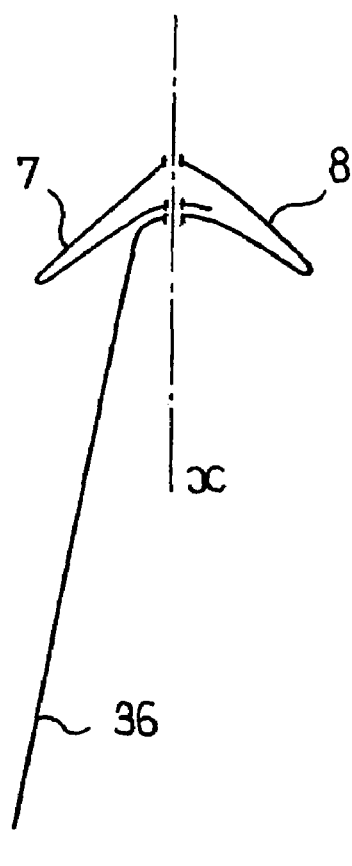
Figure 15:
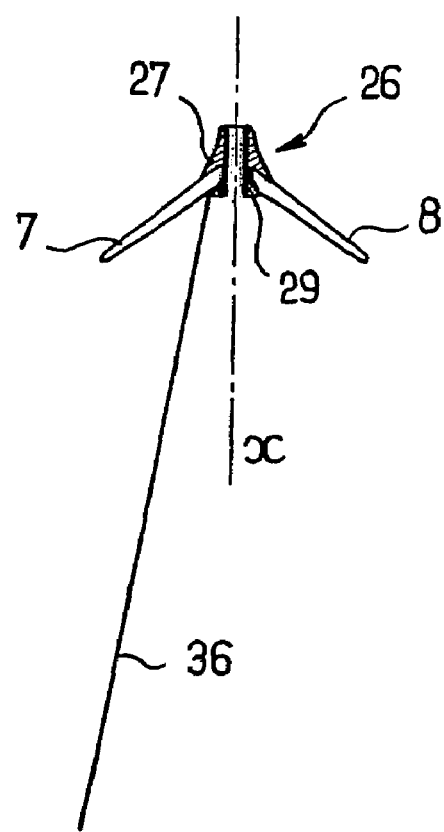

Other characteristics and advantages will become clear from the following description, given for purely illustrative and non-limitative purposes and that should be read with reference to the attached figures among which:

FIG. 1 is a diagrammatic view of details of an anchor instrument according to one embodiment of the invention, FIG. 2 is a diagrammatic view of one example of a sub urethro-cervical support according to the invention, FIGS. 3 to 7 diagrammatically show the various steps in a first method of placing a support device, FIG. 8 is a diagrammatic view of a clamp used to precisely adjust the length of the support loop, FIG. 9 is a diagrammatic view of details of an anchor instrument according to a second embodiment of the invention, FIG. 10 shows a trocar like that used in a second embodiment of a support device, FIG. 11 is a diagrammatic view of a variant of a clamp used to position a "clipping" element designed to connect the two striplets together to form a support loop, FIG. 12 shows an example of such a "clipping" element, FIG. 13 shows an example of an end piece that will be used for formation of an anchor element, FIGS. 14 and 15 diagrammatically show the positioning of a support striplet in the end piece in FIG. 13 to form an anchor element.

According to FIG. 1, the anchor device 2 comprises a needle 10 about two millimetres in diameter, and the end 12 of the needle that will penetrate through the tissues has a general conical shape. This needle 10 has been machined close to its end 12 so as to form a bearing surface 16 in the form of a ring perpendicular to its longitudinal direction. An anchor element 22 has been installed sliding on the end 12 of the needle 10 and bearing on the surface 16. This anchor element 22 is composed of a flexible washer about 3 millimetres thick and 10 millimetres in diameter made of silicone reinforced with polypropylene. The cone-shaped washer, which is concave towards the end 14 at which the needle 10 is manipulated, opposite the tip 12. This characteristic prevents the washer from being folded down towards the tip 12 of the needle. On the other hand, this washer is flexible enough so that it can fold down into position 22a (shown in dashed lines in FIG. 1) along the needle 10 when the needle is forced through biological tissues. One end of the autostatic polypropylene striplet 32 is fixed to the anchor element 22, for example by gluing or by any other appropriate attachment means.

FIG. 2 shows an example sub urethro-cervical support according to the invention. It comprises two anchor elements 22 and 24 in the form of two flexible silicone washers reinforced with polypropylene. Each washer 22 and 24 is connected to an autostatic striplet formed by a lattice of polypropylene meshes references 32 and 34 respectively. Each striplet 32 and 34 comprises an attachment element 42, 44. As shown in FIG. 2, the shapes of the attachment elements 42 and 44 are complementary and can fit into each other by pressing them together.

We will now describe different steps in a first method of implanting the sub urethro-cervical support device into the body of a patient.

FIG. 3 shows a first step in the implantation consisting of inserting a first anchor device 2 supporting a striplet 32. During this step, the needle 10 is initially inserted through the wall of the vagina V close the urethra U. The anchor element 22 folds down along the length of the needle. The needle 10 is pushed along the direction D between the muscles S of the sphincter and towards the venous plexus P.

Figure 4:
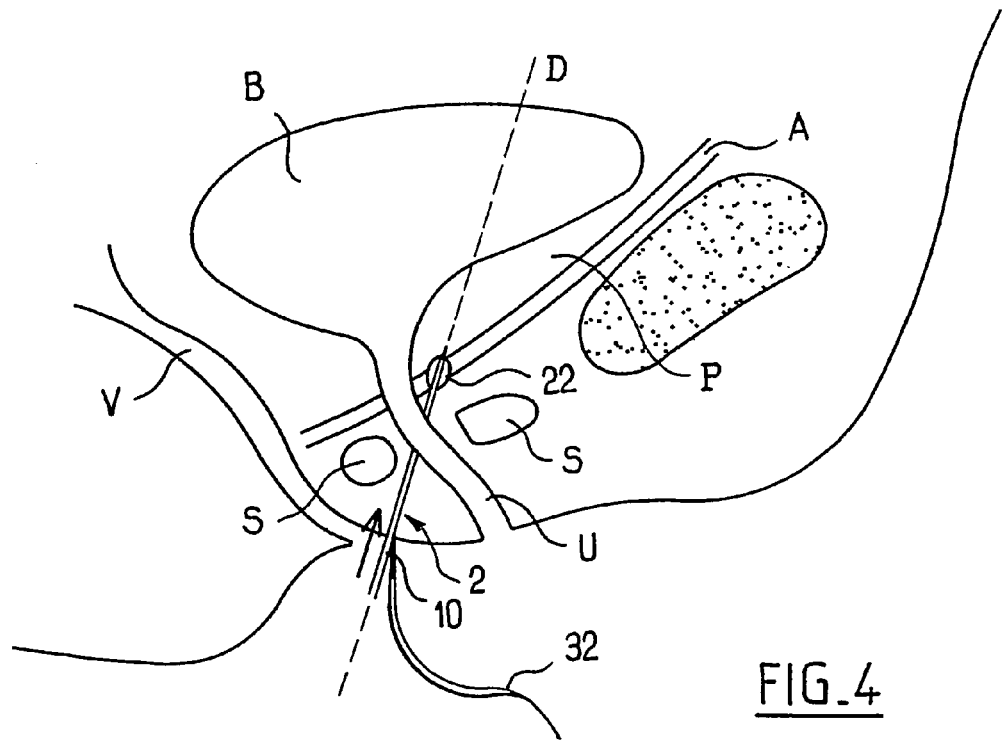

FIG. 4 shows a second step during which the needle 10 passes through the fascia of pelvic muscles A, in other words the membrane composed of dense conjunctive fibres that surrounds the muscles of the sphincter. At this moment, the surgeon may feel when he passes through a part in which the tissues are not as soft. He then stops pushing the needle 10.

As shown in FIG. 5, the needle 10 is pulled out along the direction D, which deploys the anchor element 22, the edges of which bear on the surface of the fascia of pelvic muscles A. When the surgeon withdraws the needle 10, the anchor element 22 is deployed and bears on the fascia surface A, which prevents it from being pulled along by needle 10. The anchor element 22 is then separated from the needle 10 and remains "anchored" on the fascia A. The striplet 32 fixed to its end is thus held in place.

As shown in FIG. 6, the same operation is restarted with a second anchor device 4 supporting a striplet 34. This anchor device 4 is inserted through the wall of the vagina V in the direction of the venous plexus P, but on the other side of the urethra U from the first strip 32 already in place. The two parts of the strips 32 and 34 positioned in this way then pass on each side of the urethra U. As shown in FIG. 7, the surgeon then connects the two ends of the striplets and adjusts the length of the striplet between the two anchor devices 22 and 24 and therefore the pressure exerted by these striplets at the urethra U. The two striplets 32 and 34 are then connected to each other by clipping means 42 and 44 to form a support loop under the urethra U.

Obviously, these striplets 32 and 34 could be connected differently. They could be stapled, sutured or attached by any other appropriate means. Since the urethra is a fragile organ, the attachment will preferably be made as far as possible from the urethra U to avoid the risk of damaging it. Consequently, the two striplets 32 and 34 are cut to different lengths.

In one variant of this method of implanting the support device, the striplets 32 and 34 are surrounded by a flexible sheath typically made of a sheet of plastic material that facilitates sliding during the steps in which the needles shown in FIGS. 4 and 6 are inserted. These sheaths are withdrawn by sliding along the striplets when the striplets are in place in the patient's body.

The sheaths have the advantage that they facilitate introduction of the striplets, which are autostatic. The sheaths also have the advantage that they protect the striplets during placement and prevent contamination by bacteria in the regions through which they pass.

FIG. 8 shows an example of a clamp that makes it easy to adjust the length of the loop composed of the two striplets 32 and 34. The clamp 50 is composed of two arms 52 and 54 articulated at an axis 56. The arm 52 has two ends 62 and 72 and the arm 54 has two ends, 64 and 74. The ends 62 and 64 forming a lever that the surgeon uses to tighten the clamp and the ends 72 and 74 form the tightening "jaws". There is a slit 82 or 84 at each end 72 and 74 forming the jaws, the slit being open laterally and one of the striplets 32 and 34 can slide through it.

One of the striplets 34 has an attachment element 42 at a predetermined length that is positioned on one of the jaws 72 of the clamp. The other striplet 34 passes through the slit of the opposite jaw 74. The surgeon can slide the striplet 34 through the slit 84 so as to adjust the length of the support loop passing under the urethra U. When he has found the right length, he closes the clamp 50 so as to tighten the attachment element 42 of the strip 32 onto the strip 34 at an appropriate position.

FIG. 11 shows a variant clamp. This clamp 51 is composed of two arms 52 and 54 articulated at an axis 56. The arms 52 and 54 have two ends 62, 72 and 64, 74 respectively. The ends 72 and 74 forming the clamping jaws have generally cylindrical shaped cavities adapted to hold "clipping" elements references 42 and 44. When the surgeon wants to attach the two strips 32 and 34 together to form the support loop, he superposes them and positions the jaws 72 and 74 of the clamp 51 transversely to the striplets 32 and 34, on each side of them.

FIG. 12 more precisely shows a non-limitative example of press-stud type clipping elements 42 and 44. Element 42 is in the general shape of a perforated washer, while element 44 is in the general shape of a washer fitted with a stud. The stud can perforate strips 32 and 34 and can be engaged and fixed into the orifice of element 42. Consequently, the stud has a straight section with a dimension smaller than the perforation of the washer 42, over most of its length, but it has a flared head with a larger cross-sectional dimension that this perforation.

In one embodiment of the invention shown in FIG. 1, the needle 10 is hollow and forms a duct extending between its ends 12 and 14. A syringe 18 may be connected to the opening of the duct located at the end 14 of the needle 10. This syringe 18 may be filled with an anaesthetic product. During the step shown in FIG. 3 that consists of making the needle 10 penetrate into the body of the patient, the surgeon pushes on the piston of the syringe 18. He injects the anaesthetic product through the duct formed by the needle 10 to apply a progressive local anaesthetic as the needle 10 penetrates through the body of the patient.

This embodiment of the invention is particularly advantageous since the surgeon can apply an extremely local anaesthetic well located within the patient's body. It also has the advantage that it enables the surgeon to detect if he reaches the bladder B. The surgeon does this by pulling slightly on the piston of the syringe 18. If the piston resists, then the end 12 of the needle 10 is located in a zone of tissues. In this case, the surgeon deduces that he has not penetrated the wall of the bladder B. However, if the piston starts moving and the syringe absorbs liquid, then the end 12 of the needle 10 must have penetrated the bladder B. In this case, he must stop penetration and start to withdraw the needle 10.

Consequently, the surgeon simply needs to push and to pull the piston of the syringe 18 alternately to apply the anaesthetic while continuously checking the position of the tip 12 of the needle 10.

To detect whether or not he has reached the bladder B, the surgeon can also inject a coloured liquid into the bladder. In this way, the contents of the syringe 18 will be coloured when it is absorbing liquid.

Obviously, this invention is not limited to the particular embodiments that have just been described, but could be extended to any variant complying with its spirit.

For example, the sub urethro-cervical support device may include a single strip, each end of which is connected to an anchor element.

The anchor elements may comprise radial striations or folding zones so that they can be more easily folded along the needle when the needle is pushed through the tissues.

The anchor elements are not necessarily circular, they may have any shape that can be folded and anchored easily. For example, these elements may include flexible "petals", for example made of a textile material, and these petals can be folded along the needle or expanded to bear on the fascia of pelvic muscles.

As shown in FIG. 9, the anchor device 6 comprises a needle 10 about one millimeter in diameter, and the end 12 of this needle that will penetrate through the tissues has a generally conical shape. In the same way as the needle 2 in FIG. 1, this needle 6 is provided with a crown-shaped bearing surface 16 perpendicular to its longitudinal direction, near its conical end 12. An anchor element 29 has been fitted on the needle 10, bearing on the bearing surface 16. This anchor element 9 comprises a conically shaped rigid polypropylene end piece 26 with a larger diameter of about 5 millimeters. Two strip portions 7 and 8 forming ribs and the end of a polypropylene support strip 36 are fixed on the flared base of the end piece 26, for example by gluing or welding. The end piece 26 and the two ribs 7 and 8 form the anchor element 29. The two portions of strips 7 and 8 forming the ribs can be folded down along the needle 10 when it penetrates through the biological tissues and expanded when the end piece 26 has passed through these tissues.

The anchor element may be formed as shown in FIG. 13 of an end piece 26 composed of a first conical part 27 into which a second complementary tubular part 29 is rigidly inserted. There is a flared portion 25 near the bottom of the tubular part 29. As shown in FIG. 14, the end of a striplet 36 is folded into three to form two ribs 7 and 8. The three thicknesses of folded striplets are thermo-drilled along an X-axis. The striplet 36 and the ribs 7 and 8 thus formed are then positioned between the two parts 27 and 29. The part 29 is inserted into the thermo-drilled orifice passing through the thicknesses of the striplets, the striplets bearing on the flared portion 25 of the part 29. The part 29 supporting the striplets is then inserted in the part 27. As shown in FIG. 15, the striplet 36 and the ribs 7 and 8 are held in place in the end piece 26, sandwiched between the two parts 27 and 29. A needle 10 used for placement of the support device can then be inserted in the end piece 26 along the x-axis.

Similarly, an anchor element with more than two portions of strips distributed like petals around the end piece could also be used.

The anchor element may also be composed of striplets and striplet portions arranged in petal form and fused together in position. In this case, the strips and the portions will preferably be formed from a lattice of thermoplastic meshes. This type of anchor element has the advantage that it does not necessitate a rigid end piece holding the striplets together. It is required that the least hard element possible should be inserted in the region of the vagina, which is a sensitive region.

Moreover, another method of implanting a sub urethro-cervical support device uses a surgical trocar. This type of trocar is shown in FIG. 10. The trocar 100 comprises a metallic cylindrical rod 104 (or mandrel) fitted on a handle 108, terminated by a triangular tip 106 and sliding into a canula 102, of which only the tip 106 is projecting. According to this other implantation method, the trocar 100 is inserted at the vagina V close to the urethra U in the direction D as far as the fascia of pelvic muscles. The metallic rod 104 is then withdrawn from the canula 102 while the hollow needle remains in place in the patient's body. The canula 102 then forms a guide tube through which the needle 10 supporting the anchor element can be inserted. In the same way as in the steps in FIGS. 4 and 5, the needle 10 passes through the fascia of pelvic muscles A. At this moment, the surgeon can feel when he passes through less soft part of tissues, and then stops pushing the needle.

The needle 10 is then withdrawn from the canula 102, which causes deployment of the anchor element 22, 24 or 29, for which the edges or the ribs 7 and 8 bear on the surface of the fascia A of pelvic muscles. When the surgeon removes the needle 10, the anchor element deploys and bears on the surface of the fascia A, which prevents it from being pulled along by the needle. The anchor element 22, 24 or 29 then separates from the needle 10 and remains in place on the fascia A. The striplet 32, 34 or 36 fixed to it by its end is then held in place. Finally, the canula 102 is withdrawn from the patient's body, leaving the striplet in place.

The same operation can be repeated using a second anchor device supporting a striplet. The trocar 100 is inserted once again through the wall of the vagina V in the direction of the venous plexus P, but on the other side of the urethra U from the first strip already in place.

Then, in the same way as in the first embodiment described above, the surgeon connects the two ends of the striplets and adjusts the length of the strip between the two anchor devices.

This second method of placing a support device advantageously enables the anchor element 22, 24 or 29 to remain in its folded position during insertion in the canula 102. In this case, the anchor element 22, 24 or 29 cannot expand until it comes out of the canula.

Moreover, the needle 10 can advantageously be used to form a hydrodissection or an aerodissection before the support device is implanted, in other words injecting a gas or liquid into tissues to prepare a volume in which the anchor element will fit. The volume of liquid or gas thus created is more propitious to deployment of the anchor element.

Finally, elements necessary for implantation of a sub urethro-cervical support according to the invention may advantageously be proposed to the surgeon in the form of a surgical "kit" containing all or some of the following elements: the sub urethro-cervical support device including the striplets possibly surrounded by a sheath and two anchor elements, the anchor needle(s), a device for attaching the striplets to each other, a clamp for placing the attachment element, and a trocar.

The invention claimed is:

1. A surgical instrument for implantation of a sub urethro-cervical support comprising:
   two striplets and two anchor devices, each anchor device including a needle in which the penetrating end supports a flexible anchor element, each anchor element being connected to one end of one of the striplets and can be turned down over the length of the needle while the needle is passing through biological tissues and deployed when the needle has passed through these tissues, and the striplets can be connected together by complementary attachment elements to form a supporting loop under the urethra, wherein the anchor elements have a conically shaped end piece, and at least two portions of striplets forming ribs, each of the at least two portions of striplets being part or not of each striplet, the conically shaped end piece comprising two rigid parts that can be inserted one into the other, between which said striplets or portions of striplets are held.

2. The instrument according to claim 1, wherein the needle has a bearing surface supporting the anchor element, close to the penetrating end of the needle.

3. The instrument according to claim 1, wherein the needle is hollow and forms a duct opening up at the two ends of the needle.

4. The instrument according to claim 1, wherein the striplets are surrounded by a protective sheath.

5. A sub-urethral-cervical supporting device, comprising: two striplets, two anchor devices, each anchor device and a connection means to connect the two striplets together, each anchor device being capable to be turned down over the length of a needle while the needle is passing through biological tissues and deployed when the needle has passed through these tissues and each anchor device being connected to one end of a striplet, wherein the anchor devices have a conically shaped end piece, and at least two portions of striplets forming ribs, each of the at least two portions of striplets being part or not of each striplet, the conically shaped end piece comprising two rigid parts that can be inserted one into the other, between which said striplets or portions of striplets are held.

6. The device according to claim 5, wherein the anchor elements comprise striplet portions arranged and fused together in position.

7. The device according to claim 5, wherein each striplet is made of polypropylene.

8. A surgical instrument for implantation of a sub urethro-cervical support comprising:
at least one needle with a penetrating end, two anchor elements, each of these anchor elements can be located on the penetrating end of the needle and can be turned down over the length of the needle while the needle is passing through the biological tissues and deployed when the needle has passed through these tissues, two striplets, each anchor element being connected to an end of one striplet, each of these striplets can be connected to the other striplet using complementary attachment elements to form a supporting loop under the urethra, the assembly of the striplets and of the complementary attachment elements also comprising a clamp capable of tightening the complementary attachment elements on the striplets, wherein the anchor elements have a conically shaped end piece, and at least two portions of striplets forming ribs, these portions of striplets being part or not of each striplet, the conically shaped end piece comprising two rigid parts that can be inserted one into the other, between which said striplets or portions of striplets are held.

9. The surgical assembly according to claim 8, further comprising: a trocar that comprises a canula capable of housing the needle supporting an anchor element.

10. A process for implantation of a sub urethro-cervical support device including two anchor elements, two striplets, and connection means to connect the two striplets together, each anchor element being connected to one end of a striplet, wherein the anchor elements have a conically shaped end piece, and at least two portions of striplets forming ribs, these portions of striplets being part or not of each striplet, the conically shaped end piece comprising two rigid parts that can be inserted one into the other, between which said striplets or portions of striplets are held, comprising:
inserting said striplets or said portions of striplets between two rigid parts from said conically shaped end piece of one of said two anchor elements;
inserting the one said anchor element with a needle to which an end of one of said striplets is connected, through the vagina and on a first side of the urethra to the fascia of pelvic muscles;
passing the said one anchor element through the fascia of pelvic muscles;
pulling out the needle to deploy said one anchor element on the surface of the fascia pelvic muscles;
repeating the preceding steps for a second one of said anchor elements; and
connecting the striplets together to form a supporting loop under the urethra.

* * * * *